United States Patent
Bennett

(10) Patent No.: US 9,414,974 B2
(45) Date of Patent: Aug. 16, 2016

(54) DISPOSABLE STORAGE CONTAINER FOR INFANT CLEANING TOILETRIES

(71) Applicant: David Jonathan Bennett, Johannesburg (ZA)

(72) Inventor: David Jonathan Bennett, Johannesburg (ZA)

(*) Notice: Subject to any disclaimer, the term of this patent is extended or adjusted under 35 U.S.C. 154(b) by 0 days.

(21) Appl. No.: 14/404,302

(22) PCT Filed: Dec. 20, 2013

(86) PCT No.: PCT/ZA2013/000095
§ 371 (c)(1),
(2) Date: Nov. 26, 2014

(87) PCT Pub. No.: WO2014/100840
PCT Pub. Date: Jun. 26, 2014

(65) Prior Publication Data
US 2015/0136784 A1    May 21, 2015

(51) Int. Cl.
| | |
|---|---|
| *B65D 30/00* | (2006.01) |
| *A61F 13/551* | (2006.01) |
| *A61F 15/00* | (2006.01) |
| *B65D 75/32* | (2006.01) |
| *B65D 75/58* | (2006.01) |
| *B65D 83/08* | (2006.01) |
| *A45C 11/00* | (2006.01) |

(52) U.S. Cl.
CPC .......... *A61F 13/5519* (2013.01); *A61F 15/001* (2013.01); *B65D 75/323* (2013.01); *B65D 75/5883* (2013.01); *B65D 83/0805* (2013.01); *A45C 2011/007* (2013.01); *B65D 2575/565* (2013.01); *B65D 2575/586* (2013.01)

(58) Field of Classification Search
CPC ........... B65D 81/3261; B65D 81/3266; B65D 81/3272; A61J 1/10; A45D 33/005; A45D 33/00; A45D 34/00; A45D 34/06
USPC ........................................... 220/520
See application file for complete search history.

(56) References Cited

U.S. PATENT DOCUMENTS

| | | | |
|---|---|---|---|
| 6,068,820 A | 5/2000 | De Guzman | |
| 6,601,737 B1 * | 8/2003 | Sandler | 222/192 |
| 7,234,630 B2 * | 6/2007 | Wang | 229/120.31 |
| 7,497,351 B2 * | 3/2009 | Amundson | A47K 10/421 221/135 |
| 2001/0035416 A1 * | 11/2001 | Dodson | A47K 10/421 220/524 |
| 2003/0047467 A1 * | 3/2003 | Smith et al. | 206/221 |

FOREIGN PATENT DOCUMENTS

| | | |
|---|---|---|
| DE | 3744438 A1 | 7/1989 |
| DE | 202009010543 U1 | 1/2010 |

* cited by examiner

Primary Examiner — Jeffrey Allen

(57) ABSTRACT

A disposable infant toiletry storage container, the container comprising at least two storage compartments, which are separated from one another to prevent mixing of its toiletry con-tents, wherein the container is at least partially collapsible and each compartment is sealable.

20 Claims, 1 Drawing Sheet

DISPOSABLE STORAGE CONTAINER FOR INFANT CLEANING TOILETRIES

The present invention relates to a disposable storage container for infant cleaning toiletries containing at least two such toiletries.

BACKGROUND

Infant toiletries traditionally comprise a number of different products which are required for both cleaning and conditioning the infant. These include wet tissues known as wet-wipes, various types of creams and lotions, disinfectant solutions, diapers and diaper disposal packets.

When changing the diaper of an infant, several of the aforementioned products are required simultaneously such as wet-wipes, moisturizing lotion and a new diaper. Dispensing or obtaining these products, as the case may be, is usually done with one hand by the person changing the diaper as the other hand is required for securing the infant. At such times it is often difficult, if not traumatic, for the changer to complete the task in the most expeditious and simplest manner. This difficulty is further exacerbated by the infant crying and requiring a bottle further distressing the changer.

Typically, even in the event that an infant has a changing area with all the required toiletries set-up for the changer, these toiletries need to be accessed individually by the changer for example, opening a tube of cream; opening a packet of wet-wipes and removing them; and taking a new diaper from its storage packet. Often however, the required toiletries are scattered and the task of accessing them is thereby made more difficult. Of particular relevance to the invention is cases, where the infant is travelling and requires a diaper change in an environment not having all the toiletries laid out—whereby this problem is further exacerbated. This scenario often results in the changer frantically searching or all the required toiletries, laying them out an accessing them. The use of one-handed lotion dispensers does alleviate some of the abovementioned problems, however they are not suitable for travel as the contents are easily dispensed which would spill into the infant toiletry bag.

Further, travel size toiletries are typically small in size relative to standard toiletries. As a result the individual toiletries, when not placed in a contained area of a carrier bag—tend to roll around the bag and often make rapid location of the toiletries somewhat difficult. In addition, infant toiletries are typically stored in containers which are non-deformable and not transparent. As such, it is not possible to gage the quantity of contents remaining without opening the container. Even with transparent containers—solid colored lotions cover the internal walls of the container thereby preventing the quantity of contents to be assessed by simply looking or squeezing the container.

It is an object of the invention to at least partially ameliorate the abovementioned disadvantages associated with locating and accessing infant changing toiletries. In particular, the invention seeks to facilitate a one-handed accessing of numerous toiletries, which are stored in a disposable but multi-use storage container.

SUMMARY OF THE INVENTION

A disposable infant toiletry storage container, the container comprising at least two storage compartments, which are separated from one another to prevent mixing of its toiletry contents, wherein the container is at least partially collapsible and each compartment is sealable.

Conveniently, at least two storage compartments are at least partially collapsible.

Conveniently the storage compartments are accessible and releasably sealable using a single-handed release mechanism to open a cover, which defines the compartment seal.

Preferably each compartment comprises a separate cover, which is independently accessible and releasably sealable. The user may thereby elect to only use selected products stored therein.

Preferably the compartments are substantially watertight when the cover is in a closed position thereby preventing liquid contents from evaporating from or spilling out of the compartments and foreign contaminants entering the compartments during storage.

Preferably the compartments are releasably sealable, wherein the cover and the compartment releasably engage by any one of a press-release means, a snap-fit means, or a biasing means. In the case of the press-release means, the user simply presses a locking means to release the cover, which may subsequently be lifted by the user. In the case of the snap-fit means, the user applies an upward lifting force on the cover while simultaneously applying a downward force with another part of his hand on to the container. In the case of a biasing means, the cover may be biased to either the open or closed position and have an obstructing means to maintain it in the position opposite to the relaxed position.

Conveniently the storage container comprises a combination of at least any two of the following: wet-wipes, infant lotion, infant cream, diapers, diaper disposal packets, hygiene solution or pacifier.

Conveniently, the infant toiletry storage container comprises a handle means.

Conveniently, the handle means comprises any one of an aperture through which a user passes his fingers or a protruding handle.

DETAILED DESCRIPTION OF THE INVENTION

Figure 1:
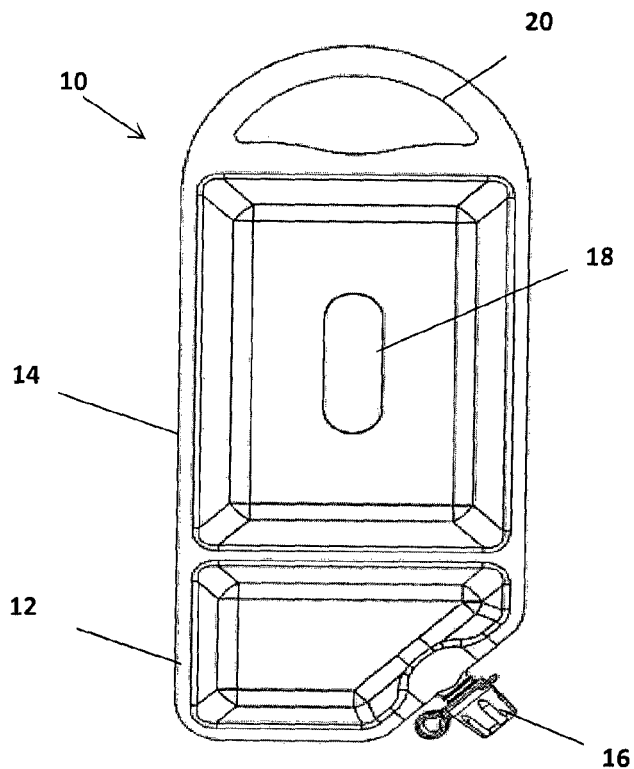
FIG. 1 is a top planar view of an infant toiletry storage container of the invention.
Figure 2:
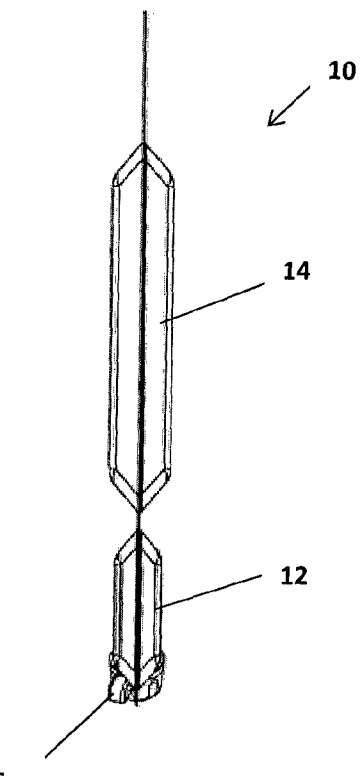
FIG. 2 is a side planar view of the storage container of FIG. 1.
Figure 3:
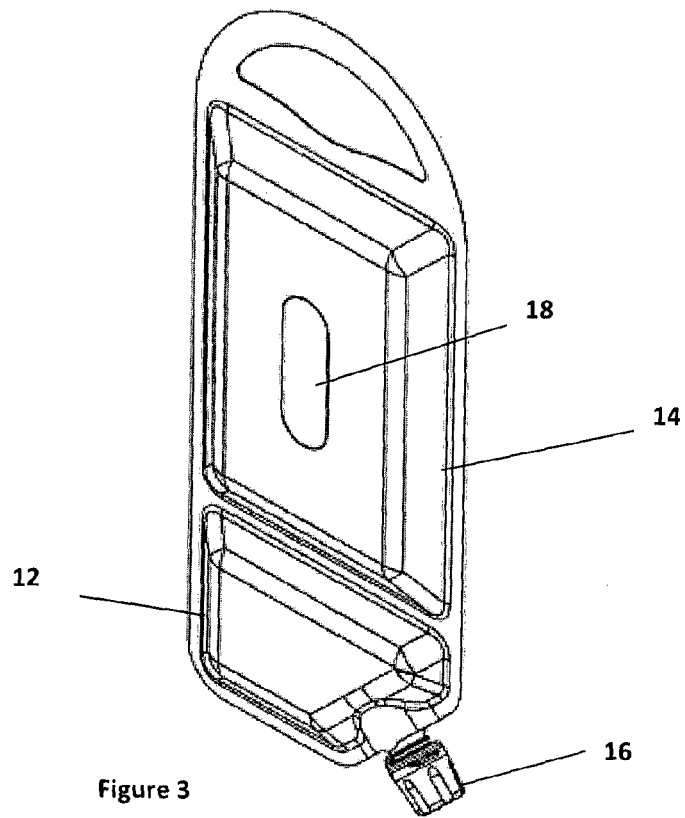
FIG. 3 is front perspective view of the storage container of FIG. 1.

FIGS. 1 to 3 of the invention show an infant toiletry storage container 10 comprising two compartments 12, 14. The compartments are separated to prevent mixing of contents between the containers. The container is substantially rectangular when in an inflated condition and viewed from a top planar view. The container is formed from a plastics material which is collapsible. The individual compartments 12, 14 are maintained in an inflated condition by the counter-force which the container contents exert against the internal container walls, in use. A user can thereby determine the volume of contents remaining in each compartment by simply viewing the inflation level of the compartments.

The first compartment stores infant lotion and is dispensable through a dispenser 16 located at corner on the outer perimeter of the container. The dispenser comprises a nozzle with a lid, which lid is removably securable on to the nozzle. In use, the user would remove the lid from nozzle to dispense lotion and secure the lid back on to the nozzle to prevent leaking of contents.

The second compartment stores infant sanitary wipes, which are dispensable through an elongate aperture located substantially across the top central portion of the second compartment. A self-adhesive peel-tab 18 covers the aperture and is releasably securable over the aperture to enable a user to remove wipes and thereafter close the aperture. In doing so, the contents of the storage container remain in the intended condition without evaporation or spilling. Further, unwanted contaminants do not enter the compartments when the toiletries are not being used.

A semi-circular aperture 20 located proximal to the second compartment defines a handle through which a user can pass his fingers to carry the container.

It will be appreciated that the invention is not limited to the abovementioned embodiments. For example the container may have partially rigid frame into which individual containers are insertable, alternately facilitate the use of a rigid lid. The lotion dispenser may have a screw cover or snap-fit lid. The sanitary wipes cover may comprise a rigid lid which is secured on to the second compartment and over the dispensing aperture. Also, the storage container may include a third toiletry such as a hygiene solution, diaper container or diaper disposal packet. To this extent, for the purposes of the invention, a toiletry is defined as anything associated with facilitating the cleaning of an infant and the disposal of waste products resulting from such cleaning.

The summary of invention and claims form an integral aspect of the description of the invention.

The invention claimed is:

1. A disposable infant toiletry storage container, the container comprising:
   an outer edge defining a perimeter of the disposable infant toiletry storage container;
   a first storage compartment having a first perimeter disposed within the outer edge and not in contact with the perimeter, the first storage compartment configured to store a liquid;
   a dispenser disposed on a corner portion of the outer edge;
   a second storage compartment for storing sanitary wipes, the second storage compartment including an elongate aperture located between an outer perimeter of the second storage compartment, the first storage compartment and the second storage compartment are separated from one another to prevent mixing of its toiletry contents, wherein the container is at least partially collapsible and each compartment is sealable; and
   a handle adjacent to the second storage compartment,
   wherein the dispenser includes a nozzle and is configured to dispense the liquid from the first storage compartment.

2. The infant toiletry storage container as claimed in claim 1, wherein the first and the second storage compartments are at least partially collapsible.

3. The infant toiletry storage container as claimed in claim 1, wherein the first and the second storage compartments are accessible and releasably sealable using a single-handed release mechanism to open a cover.

4. The infant toiletry storage container as claimed in claim 1, wherein the first and the second storage compartments comprise a separate cover, which is independently accessible and releasably sealable.

5. The infant toiletry storage container as claimed in claim 1, wherein the first and the second storage compartments are substantially watertight when a cover is in a closed position.

6. The infant toiletry storage container as claimed in claim 1, wherein a cover and at least one compartment releasably engage by any one of a press-release means, a snap-fit means, or a biasing means.

7. The infant toiletry storage container as claimed in claim 1, wherein the storage container comprises a combination of at least any two of the following: wet wipes, infant lotion, infant cream, diapers, diaper disposal packets, hygiene solution or pacifier.

8. The infant toiletry storage container as claimed in claim 2, wherein the first and the second storage compartments are accessible and releasably sealable using a single-handed release mechanism to open a cover.

9. The infant toiletry storage container as claimed in claim 2, wherein the first and the second storage compartments comprise a separate cover, which is independently accessible and releasably sealable.

10. The infant toiletry storage container as claimed in claim 3, wherein the first and the second storage compartments comprise a separate cover, which is independently accessible and releasably sealable.

11. The infant toiletry storage container as claimed in claim 2, wherein the first and the second storage compartments are substantially watertight when a cover is in a closed position.

12. The infant toiletry storage container as claimed in claim 3, wherein the first and the second storage compartments are substantially watertight when the cover is in a closed position.

13. The infant toiletry storage container as claimed in claim 4, wherein the first and the second storage compartments are substantially watertight when a cover is in a closed position.

14. The infant toiletry storage container as claimed in claim 2, wherein a cover and one compartment releasably engage by any one of a press-release means, a snap-fit means, or a biasing means.

15. The infant toiletry storage container as claimed in claim 3, wherein the cover and one compartment releasably engage by any one of a press-release means, a snap-fit means, or a biasing means.

16. The infant toiletry storage container as claimed in claim 4, wherein the cover and one compartment releasably engage by any one of a press-release means, a snap-fit means, or a biasing means.

17. The infant toiletry storage container as claimed in claim 5, wherein the cover and one compartment releasably engage by any one of a press-release means, a snap-fit means, or a biasing means.

18. The infant toiletry storage container as claimed in claim 2, wherein the storage container comprises a combination of at least any two of the following: wet wipes, infant lotion, infant cream, diapers, diaper disposal packets, hygiene solution or pacifier.

19. The infant toiletry storage container as claimed in claim 3, wherein the storage container comprises a combination of at least any two of the following: wet wipes, infant lotion, infant cream, diapers, diaper disposal packets, hygiene solution or pacifier.

20. The infant toiletry storage container as claimed in claim 1, further comprising a third storage compartment for storing at least one of the following: wet wipes, infant lotion, infant cream, diapers, diaper disposal packets, hygiene solution or pacifier.

* * * * *